(12) United States Patent
Meunier et al.

(10) Patent No.: US 11,679,033 B2
(45) Date of Patent: Jun. 20, 2023

(54) FRAMELESS GOGGLE

(71) Applicant: Oakley, Inc., Foothill Ranch, CA (US)

(72) Inventors: Benjamin John Meunier, San Clemente, CA (US); Dugan O'Keene, Newport Beach, CA (US); Ryan Neil Saylor, Mission Viejo, CA (US); Cameron Scott Burns, Rancho Santa Margarita, CA (US)

(73) Assignee: Oakley, Inc., Foothill Ranch (CA)

( * ) Notice: Subject to any disclaimer, the term of this patent is extended or adjusted under 35 U.S.C. 154(b) by 0 days.

(21) Appl. No.: 17/033,015

(22) Filed: Sep. 25, 2020

(65) Prior Publication Data

US 2021/0106465 A1 Apr. 15, 2021

Related U.S. Application Data

(60) Provisional application No. 62/915,357, filed on Oct. 15, 2019.

(51) Int. Cl.
*A61F 9/02* (2006.01)

(52) U.S. Cl.
CPC .............. *A61F 9/027* (2013.01); *A61F 9/026* (2013.01)

(58) Field of Classification Search
CPC . A61F 9/02; A61F 9/026; A61F 9/027; A63B 33/002
USPC ...................................................... 2/426, 452
See application file for complete search history.

(56) References Cited

U.S. PATENT DOCUMENTS

| | | | | |
|---|---|---|---|---|
| 1,188,679 A | * | 6/1916 | Rextrew | A61F 9/02 2/447 |
| 2,296,634 A | * | 9/1942 | Fink | G02C 7/16 D16/314 |
| 2,387,849 A | * | 10/1945 | Lehmberg | G02C 1/06 2/452 |
| 2,680,846 A | * | 6/1954 | Hirschmann | A61F 9/026 2/441 |
| 3,691,565 A | * | 9/1972 | Galonek | A61F 9/02 2/431 |
| 4,571,748 A | | 2/1986 | Caroll et al. | |
| 4,603,442 A | * | 8/1986 | Barfield | A61F 9/02 2/446 |

(Continued)

FOREIGN PATENT DOCUMENTS

| | | |
|---|---|---|
| GB | 2 453 109 A | 4/2009 |
| WO | 2006/106541 A1 | 10/2006 |
| WO | 2020/172398 A1 | 8/2020 |

OTHER PUBLICATIONS

Uvex Stealth Safety Goggles with Uvextreme Anti-Fog Coating, Honeywell Safety, Available via the Wayback Machine at https://web.archive.org/web/20171025010014/https://www.honeywellsafety.com/Products/Eye_and_Face_Protection/Uvex_Stealth.aspx?LangType=1033 (Archived Oct. 25, 2017); 6 pages.

(Continued)

*Primary Examiner* — F Griffin Hall
(74) *Attorney, Agent, or Firm* — Sterne, Kessler, Goldstein & Fox P.L.L.C.

(57) ABSTRACT

A frameless goggle with a lens that is structurally self-supporting without any external support from a frame, chassis, or other, similar components. The resulting goggle is more streamlined and has fewer parts to manufacture and assemble. In some embodiments, the goggle lens includes an integral support portion that improves the stiffness and strength of the lens.

25 Claims, 4 Drawing Sheets

(56) References Cited

U.S. PATENT DOCUMENTS

| | | | | |
|---|---|---|---|---|
| 4,670,914 | A * | 6/1987 | Harris | A61F 9/028 2/426 |
| 4,779,291 | A * | 10/1988 | Russell | A61F 9/02 2/439 |
| 4,850,058 | A * | 7/1989 | Cheng | A61F 9/02 2/439 |
| 5,012,527 | A * | 5/1991 | Michel | A61F 9/029 2/9 |
| 5,213,241 | A * | 5/1993 | Dewar | A45C 11/04 206/5 |
| 5,245,709 | A * | 9/1993 | Shipcott | A61F 9/027 2/425 |
| 5,752,280 | A * | 5/1998 | Hill | A42B 3/185 2/453 |
| 5,969,786 | A * | 10/1999 | Marcum | A61F 9/02 351/156 |
| 6,308,711 | B1 * | 10/2001 | Goldberg | A61F 9/02 128/858 |
| 6,511,177 | B1 * | 1/2003 | Hall | A61F 9/025 351/119 |
| 6,530,659 | B1 | 3/2003 | Marcum | |
| 6,609,255 | B2 * | 8/2003 | Lane | A61F 9/025 2/431 |
| 7,118,210 | B2 * | 10/2006 | Landers | A61F 9/045 351/123 |
| 9,655,783 | B2 * | 5/2017 | McNeal | A61F 9/027 |
| 2007/0089220 | A1 * | 4/2007 | Shiue | A63B 33/002 2/443 |
| 2009/0064398 | A1 | 3/2009 | Chou | |
| 2011/0194065 | A1 | 8/2011 | Belbey et al. | |
| 2013/0180037 | A1 | 7/2013 | Wang | |
| 2015/0205144 | A1 | 7/2015 | Chin | |
| 2017/0131563 | A1 * | 5/2017 | Shiue | A61F 9/027 |

OTHER PUBLICATIONS

International Search Report and Written Opinion, dated Dec. 4, 2020 in Related PCT Application No. PCT/US2020/052735; 20 pages.

* cited by examiner

FRAMELESS GOGGLE

BACKGROUND

Goggles are a type of eyewear that typically covers a significant portion of the face of the user beyond the eyes. Goggles usually are formed to follow the contour of the face for better protection of the eyes and face of a user. This type of eyewear is usually designed for activities that require increased protection of the user's eye and face such as snow sports, motorcycle racing, and bicycle racing.

A typical set of goggles includes a transparent lens that is supported by a separate frame component. The frame provides physical support to the lens and is usually located around the outside of the lens. The frame also provides attachment points for the goggle strap, which is typically made of a soft elastic material and is configured to go around the rear of the head of the user. Frames found on the outside of the lens make the goggles bulkier and less streamlined. The frame may also restrict the user's field of vision because frames are not optically transparent.

Recently, goggle designs have moved the frame to the interior side of the lens to achieve a "rimless" goggle. This presents a more streamlined external design of the goggle. But these interior frames must still be designed to minimize interference with the user's field of view. Further, the separate frame adds additional manufacturing and assembly complexity and cost.

BRIEF SUMMARY

A goggle according to some embodiments of the present disclosure includes a frameless lens that is self-supporting without the addition of a frame. This allows for a streamlined goggle design that minimizes additional components needed to manufacture and assemble the goggle. A goggle according to some embodiments of the present disclosure includes a lens comprising a lens body. The lens body may include a first strap attachment portion at a first end of the lens body, wherein the first strap attachment portion is configured to retain a first end of a goggle strap, and a second strap attachment portion at a second end of the lens body, wherein the second strap attachment portion is configured to retain a second end of the goggle strap. The lens body may also include a frame element, wherein the frame element is a monolithic part of the lens body, and wherein the frame element increases a stiffness of the lens when compared to an otherwise identical lens without the frame element. The lens may be structurally self-supporting without a frame, and the first strap attachment portion and the second strap attachment portion may be monolithic portions of the lens body.

A goggle according to further embodiments includes a lens and a cushion retainer located on an integral part of the lens, wherein the cushion retainer increases a stiffness of the lens when compared to an otherwise identical lens without the support portion. A cushion may be attached directly to the cushion retainer, wherein the cushion is configured to contact a face of a user when the goggle is being worn, and wherein the lens with the support portion is structurally self-supporting without a frame.

A goggle according to further embodiments includes a lens and a first strap attachment portion integrally molded at a first end of the lens, wherein the first strap attachment portion is configured to retain a first end of a strap. A second strap attachment portion may be integrally molded at a second end of the lens that is opposite the first end, wherein the second strap attachment portion is configured to retain a second end of the strap. A cushion may be attached directly to a rear surface of the lens, wherein the cushion is configured to contact a face of a user when the goggle is being worn. The lens may be structurally self-supporting without a frame, wherein the first strap attachment portion and the second strap attachment portion are not visible from a viewpoint located along a viewpoint line extending in a straight-ahead direction from the lens, wherein the viewpoint line intersects a meridian line that divides the lens into two equal portions, the meridian line extending along the front surface of the lens in a direction between a top of the lens and a bottom of the lens.

BRIEF DESCRIPTION OF THE DRAWINGS/FIGURES

DETAILED DESCRIPTION

Embodiments of the present disclosure will now be described in detail in the accompanying drawings. References to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As discussed in the Background, a typical goggle uses a frame to provide structural support for the lens. This approach results in a goggle that is less streamlined and larger than necessary because of the need to ensure that the frame does not obstruct the field of vision of the user. Furthermore, a frame is an additional element that must be manufactured and assembled with the google, which adds both complexity and cost to the goggle.

Accordingly, embodiments of the present disclosure provide a frameless goggle lens that is physically self-supporting without the need for a separate frame element. Some embodiments of the present disclosure are a lens for a goggle that includes a lens body. The lens body may include a first strap attachment portion at a first end of the lens body, wherein the first strap attachment portion is configured to retain a first end of a goggle strap, and a second strap attachment portion at a second end of the lens body, wherein the second strap attachment portion is configured to retain a second end of the goggle strap. The lens body may also include a support portion extending in a direction between the first end and the second end, wherein the support portion is an integral, monolithic part of lens body, and wherein the support portion increases a stiffness of the lens when compared to an otherwise identical lens without the support portion. The lens is structurally self-supporting without a frame, and the first strap attachment portion and the second strap attachment portion may be integral, monolithic portions of the lens body. These features allow the lens to form a goggle without a frame, presenting a more streamlined and aesthetically pleasing goggle without the additional complexity and cost of a separate frame element.

As used herein, the term "horizontal" refers to a direction substantially parallel to a direction between both eyes of an eyewear's wearer. As used herein, the term "vertical" refers to a direction substantially perpendicular to the horizontal direction and along an eyewear's lens's surface.

Figure 1:
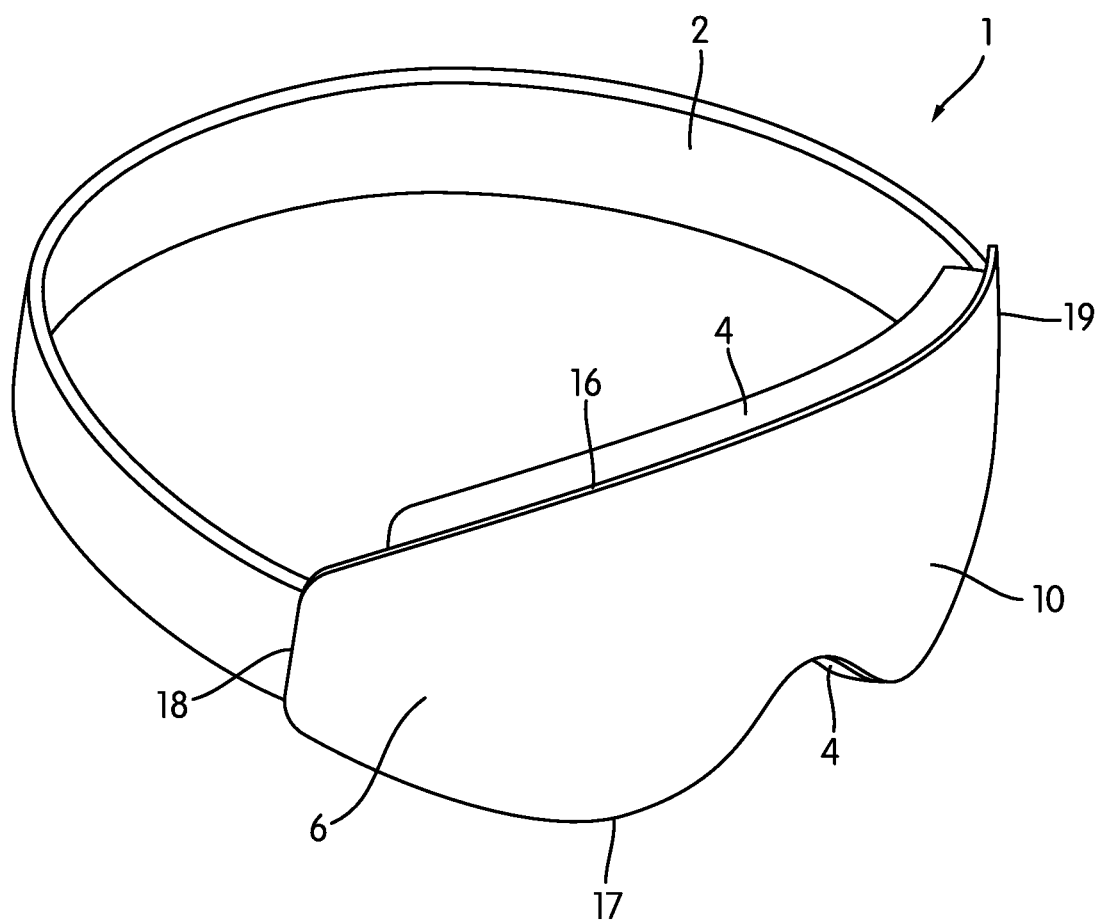
FIG. 1 is a perspective view of a frameless goggle according to embodiments.

As shown in FIG. 1, which is a perspective view of some embodiments of the present disclosure, a goggle 1 includes a strap 2 and a lens 10. Strap 2 is attached to a left side 18 and a right side 19 of goggle 1 to form a loop configured to encircle the head of a user. Strap 2 is thus configured to removably attach goggle 1 to the head of a user. Strap 2 may be made of soft elastic material, and may include elements such as buckles or clips to adjust the length of strap 2.

Figure 2:
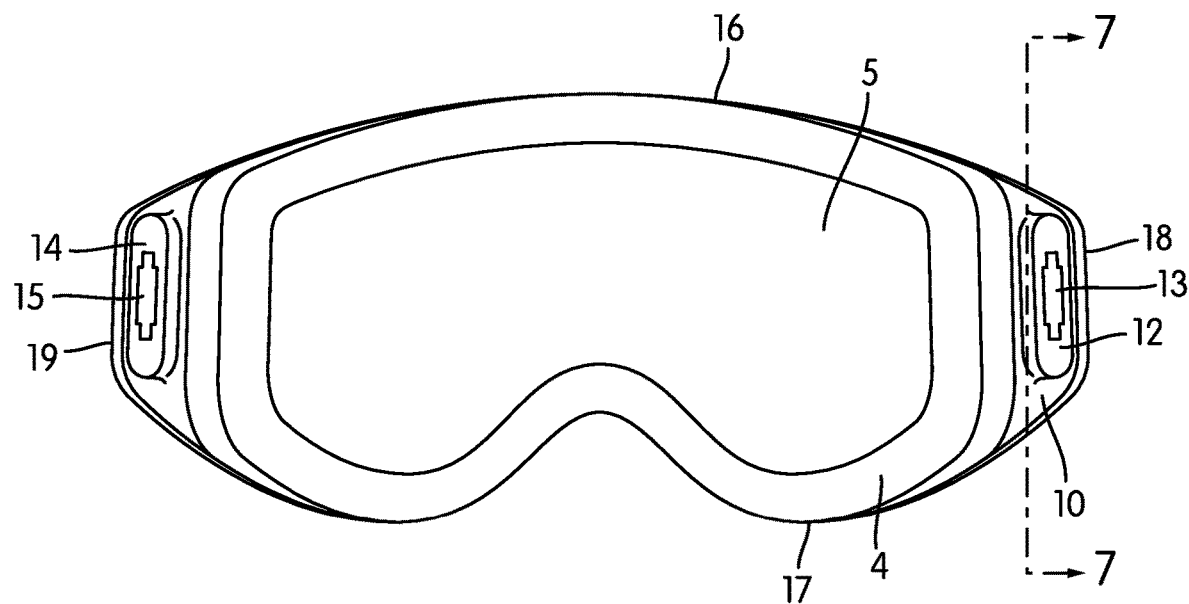
FIG. 2 is a rear view of a frameless goggle according to embodiments.

The interior or rear of goggle 1, according to some embodiments, is shown in FIG. 2, which is a rear view of goggle 1 without strap 2. In embodiments, lens 10 may include any or all features or elements that are normally found on a frame or chassis for a goggle. These frame elements or features may be integral and monolithic parts of lens 10, thus enabling lens 10 to function without a frame. As used herein, integral and monolithic means that these elements are not added-on parts of lens 10 but are present in or on lens 10 from the point of manufacture. For example, in some embodiments lens 10 may be molded, which can also refer to casting or thermoforming processes. The frame or chassis elements that are integral and monolithic with lens 10 would have been molded as part of lens 10 when lens 10 is initially created. Integrating such elements with lens 10 improves the field of view of a wearer as compared to goggles with an internal or external frame. Integrating such elements with lens 10 also improves the performance of resulting goggle 1, making goggle 1 more streamlined and aerodynamic because it does not include an additional frame. As discussed in further detail below, some embodiments of lens 10 are configured to present a smooth, streamlined shape in the outward (forward) facing direction, which is made possible by the integration of necessary frame features directly with lens 10. Moreover, integration of these features with lens 10 results in goggle 1 needing fewer total parts, which simplifies manufacturing and reduces time and expense needed to assemble lens 10. For example, in some embodiments goggle 1 may consist of five or fewer separate components that need to be assembled after manufacturing.

Figure 3:
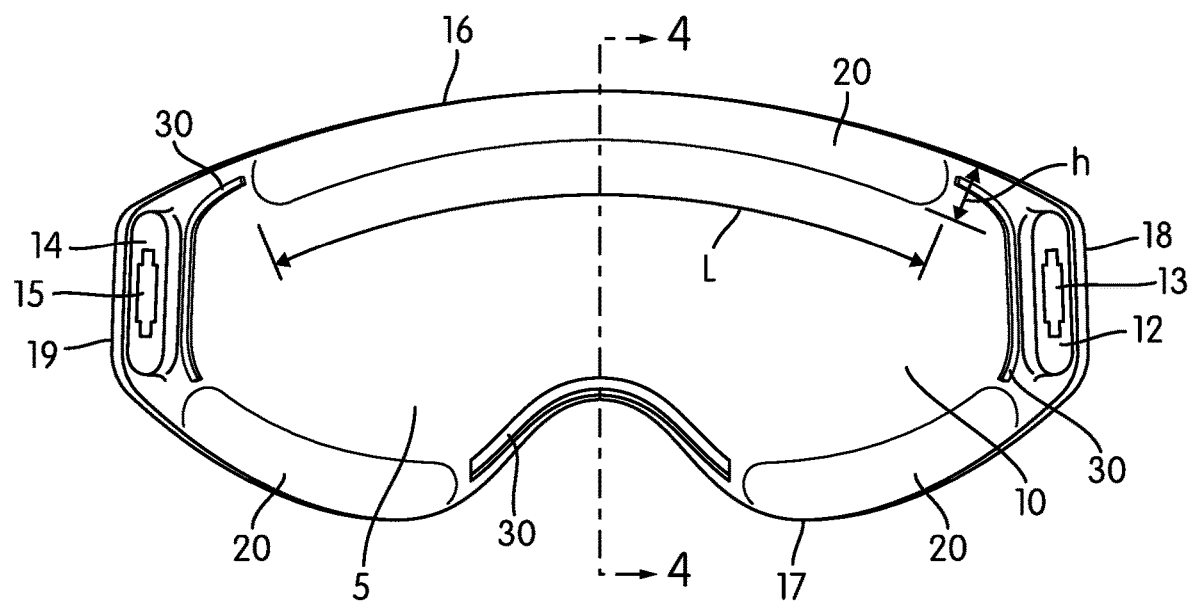
FIG. 3 is a rear view of a frameless goggle according to embodiments.

Lens 10 may include frame elements necessary to attach a faceplate or cushion 4 directly to lens 10. Accordingly, in some embodiments, lens 10 may include a cushion retainer 30, such as protrusions, grooves, channels, or recesses configured to engage with and secure cushion 4 to lens 10. For example, as shown in FIG. 3, cushion retainer 30 may be a set of grooves in lens 10 configured to engage with a matching protrusion on cushion 4 so as to secure cushion 4. In some embodiments, as shown in FIG. 3, cushion retainer 30 may be discontinuous. In other embodiments, cushion retainer 30 may form a continuous loop around lens 10, for example if cushion retainer 30 takes the form of a continuous groove on the surface of lens 10. In some embodiments, cushion 4 may be attached directly to a rear surface 5 of lens 10. Cushion 4 may be configured to contact the face of the user when goggle 1 is being worn and may be designed to improve user comfort. Cushion 4 may be made of any suitable elastic material, such as open or closed cell foam or rubber materials. Some example embodiments of cushion 4 are described in further detail in the U.S. patent application titled "Eyewear Cushion with Variable Compression and Improved Moisture Management" filed on Aug. 22, 2019 (62/915,362), the complete disclosure of which is incorporated herein by reference. As shown in FIG. 2, cushion 4 may form a closed loop around the periphery of rear surface 5 of lens 10. However, in other embodiments cushion 4 may not form a complete loop and may be discontinuous.

Figure 7:
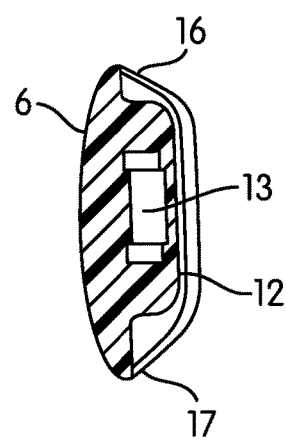
FIG. 7 is a cross section of a lens of a frameless goggle according to embodiments.

Also shown in FIG. 2 are a first strap attachment portion 12 and a second strap attachment portion 14 located on lens 10. These portions are another example of frame elements that are integral and monolithic portions of lens 10, as shown in the cross section view of FIG. 7. First strap attachment portion 12 is located near the edge of left side 18 of lens 10 and second strap attachment portion 14 is located near the edge of right side 19 of lens 10. The strap attachment portions are designed to serve as attachment points for the ends of strap 2. For example, in some embodiments, the strap attachment portions include cavities configured to receive clips of a goggle strap, as discussed below with respect to FIG. 3.

As best shown in FIG. 3, which is a rear view of goggle 1 without strap 2 and cushion 4, in some embodiments first strap attachment portion 12 and second strap attachment portion 14 may constitute protrusions that extend rearward (i.e., towards the face of the wearer) from rear surface 5 of lens 10, depressions (such as pockets or hollows) that enter into the interior of lens 10 from rear surface 5 of lens 10, or a combination of protrusions and depressions. The protrusions and/or depressions may be shaped so as to mate with the ends of strap 2. For example, the protrusions and/or depressions may be shaped as receptacles to receive or attach to corresponding components on the ends of strap 2.

In some embodiments, the ends of strap 2 include loops, and first strap attachment portion 12 and second strap attachment portion 14 constitute protrusions shaped so as to hold the loops in place.

Figure 6:
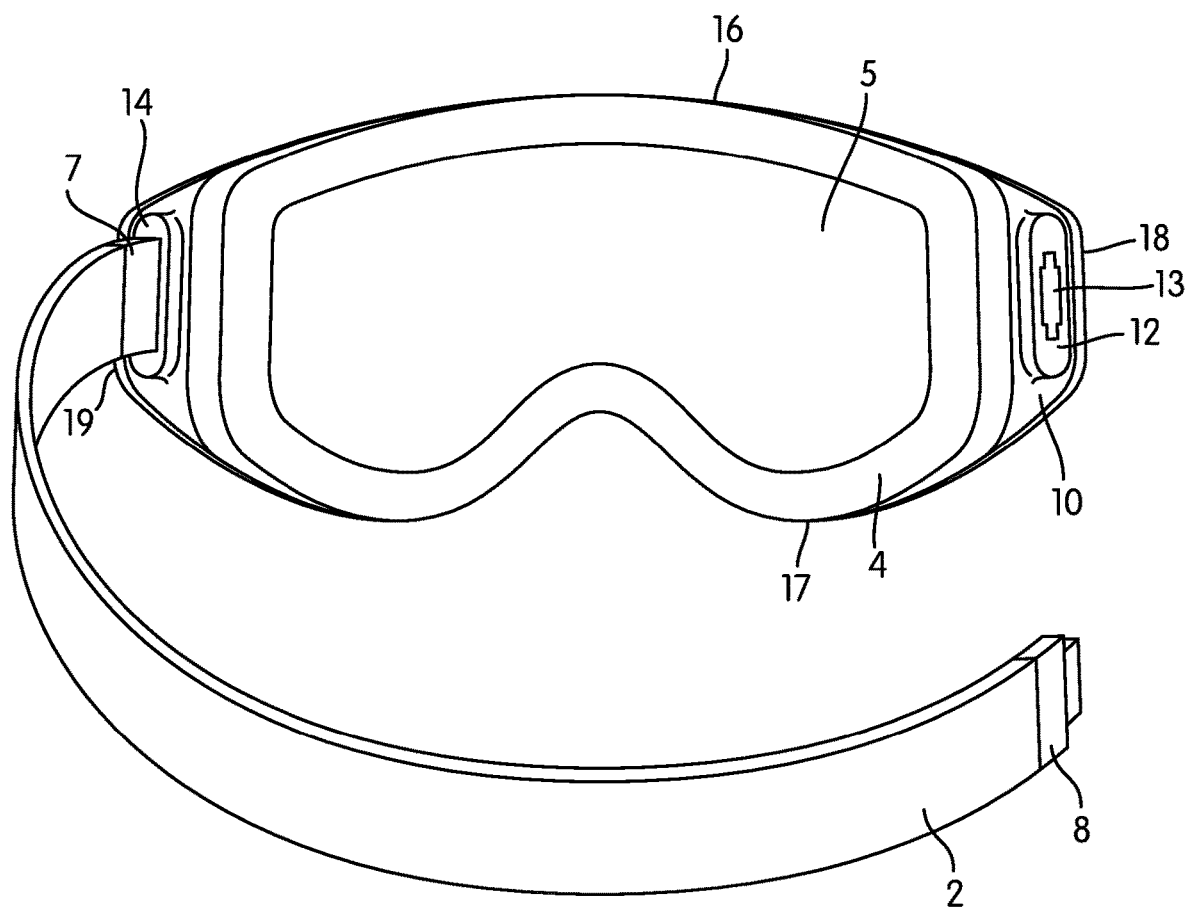
FIG. 6 is a rear view of a frameless goggle according to embodiments.

In some embodiments, each end of strap 2 has a strap attachment component that is configured to be inserted into the respective receptacles (13, 15) of first strap attachment portion 12 and second strap attachment portion 14. For example, each of first strap attachment portion 12 and second strap attachment portion 14 may include a protrusion and/or depression shaped as a clip, a post, a latch, a housing, a catch, a slot, a clasp, a hollow body, a flange, or the like, configured to mate with corresponding features on the ends of strap 2, as shown in FIG. 6. In some embodiments, each of first strap attachment portion 12 and second strap attachment portion 14 may be cavities that are configured to form an interference/snap fit with the corresponding components on the end of strap 2. For example, as shown in FIG. 6, each of first strap attachment portion 12 and second strap attachment portion 14 may be shaped like a buckle receiver for receiving a respective buckle-shaped component 7, 8 at each end of strap 2, similar to how the end of a seatbelt is inserted into a seat belt buckle. Like a seat belt buckle, first strap attachment portion 12 and second strap attachment portion 14 may include features such as levers, latches, or buttons that serve to releasably retain the ends of strap 2. In another example, first strap attachment portion 12 and second strap attachment portion 14 may include slots or through-holes cut through lens 10 that allow the ends of strap 2 to pass through the lens and double back to a clip or buckle on strap 2. These embodiments of lens 10 have the advantage of allowing the strap to be easily and quickly removed and replaced as desired.

The shape of first strap attachment portion 12 and second strap attachment portion 14 may also reverse the disposition of the elements described above: each end of strap 2 may have an attachment receptacle, and first strap attachment portion 12 and second strap attachment portion 14 may have a corresponding protrusion or other element for insertion into the receptacles on the respective ends of strap 2. The specific shape and sizing of the receptacles and insertion elements may be varied as needed to meet the specific design goals.

The frame-type elements of lens 10 are integrally formed, monolithic portions of lens 10. Thus, in the above embodiments, first strap attachment portion 12 and second strap attachment portion 14 are integrally formed, monolithic portions of lens 10 and are not disposed on a separate element that is glued, adhered, or otherwise fastened to lens 10. That is, first strap attachment portion 12 and second strap attachment portion 14 form a single, monolithic structure with lens 1, and can be made of the same material as lens 1. Lens 1 with integrated strap attachment portions 12 and 14 may be made using any suitable method known in the art. For example, lens 1 with integrated strap attachment portions 12 and 14 may be molded, which as used herein includes processes such as casting or thermoforming. In embodiments, strap attachment portions 12 and 14 may be formed simultaneously with and/or during the same process as lens 1, or may be added in a chemical bonding process that integrates attachment portions 12 and 14 with lens 1 such that no seam can be detected.

Other embodiments of first strap attachment portion 12 and second strap attachment portion 14 may include other releasable or non-releasable strap attachment elements adhered or otherwise secured to the inner surface of lens 10. For example, first strap attachment portion 12 and second strap attachment portion 14 and the ends of strap 2 may include non-integral buckles similar to those found on life jackets to enable the releasable attachment of strap 2.

Figure 5:
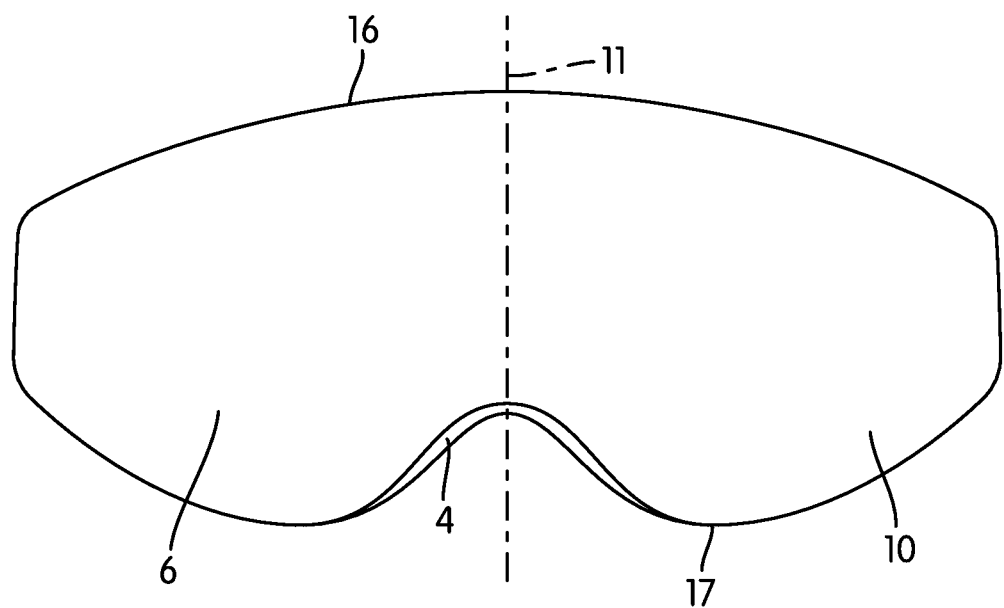
FIG. 5 is a front view of a frameless goggle according to embodiments.

In some embodiments of goggle 1, first strap attachment portion 12 and second strap attachment portion 14 are not visible when goggle 1 is viewed from straight ahead (i.e. a front view), such as by an observer standing in front of the wearer. This view is taken from a viewpoint, which is shown, for example, in FIG. 5, that is defined as a point along a line that is perpendicular to both a meridian line 11 and a front surface 6 of lens 10 that meridian line 11 passes through. Meridian line 11 is defined as a line that extends from top 16 to bottom 17 and divides lens 10 into two equal portions. Meridian line 11 also lies on front surface 6 of lens 10. Thus, the viewpoint line for the straight ahead view extends directly away from lens 10 along a plane that divides lens 10 into two equal portions. The curvature of lens 10 and the design and placement of first strap attachment portion 12 and second strap attachment portion 14 means that the attachment portions are not visible from a viewpoint on the defined viewpoint line because they are obscured by the lens material. In these and other embodiments of lens 10, neither first strap attachment portion 12 nor second strap attachment portion 14 are visible to a user wearing goggle 1.

Because goggle 1 does not include a frame, lens 10 is configured to be structurally self-supporting. Specifically, the body of lens 10 is sufficiently stiff and has a desired impact resistance without support from a separate frame or chassis. The lateral stiffness of lens 10, which is the resistance to bending between left side 18 and right side 19, is particularly important because strap 2 is attached to, and pulls on, left side 18 and right side 19 of lens 10. Accordingly, it is desirable to reduce flexing induced by the force of strap 2 on left side 18 and right side 19 to ensure a proper fit of goggle 1. Reducing flexing of lens 10 also reduces the likelihood of performance-diminishing optical distortions that would result from bending the lens.

In some embodiments, lens 10 is structurally self-supporting without any additional elements being part of lens 10. For example, lens 10 may be made of any of a variety of optical materials including glasses or plastics such as acrylics or polycarbonates. Certain materials used for lens 10 may possess sufficient strength and stiffness such that lens 10 requires no further reinforcement from structures exterior to lens 10, such as external frames.

Figure 4:
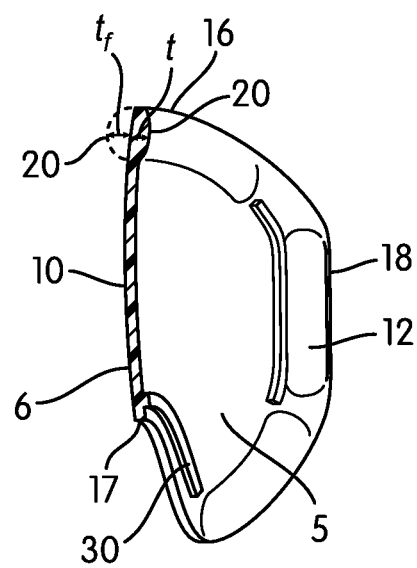
FIG. 4 is cross section of a lens of a frameless goggle according to embodiments.

Various frame elements that are incorporated into lens 10 may be configured to increase the stiffness of lens 10 in addition to performing other functions. For example, the first strap attachment portion 12 and second strap attachment portion 14 may increase the stiffness of lens 10 in addition to being configured to, for example, act as attachments for strap 2. Cushion retainer 30 is another example of a frame element that may also act to stiffen lens 10 in addition to helping retain cushion 4. For example, the size, shape, dimensions (height, length, thickness or depth) of cushion retainer 30 can be selected to stiffen lens 10 as desired while also acting to retain cushion 4. For example, cushion retainer 30 may include protrusions or extrusions on the surface of lens 4 that retain cushion 4 and also act to stiffen lens 4. As viewed in cross-section as shown in FIG. 4, these protrusions may be shaped as portions of a square extending from the surface, but may also have any desired shape, including circles, ovals, rectangles, pyramids, or any other desired polygonal shape.

In some embodiments, lens 10 may also include a support portion 20 as shown, for example, in FIG. 3. Support portion 20 is another example of a frame element that increases stiffness of lens 10. Support portion 20 is configured to increase the strength and stiffness of lens 10. Lens 10 with support portion 20 is stiffer and stronger than an otherwise identical goggle lens without support portion 20. In some embodiments, the inclusion of support portion 20 into lens 10 enables lens 10 to be structurally self-supporting. Support portion 20 may be configured in a variety of different arrangements to meet the design goals of lens 10. For example, as shown in FIG. 3 and in the cross-section view of FIG. 4, support portion 20 may be a single thickened portion of lens 10 that stretches laterally between left side 18 and right side 19 across lens 10 in the horizontal direction. In these embodiments, lens 10 is thicker in support portion 20 than outside of support portion 20. For purposes of this disclosure, "thickness" is measured in the locally perpendicular direction between front surface 6 and rear surface 5 at any point on lens 10. This measurement, is shown, for example, as thickness "t" in the cross section view of FIG. 4, where the exemplary thickness is taken near the top of lens 10. For example, in some embodiments a thickness of lens 10 near an ocular region, which is the region of lens 10 corresponding with a field of view of a wearer (i.e. in the line of sight of the wearer), may be between 1.75 mm and 2.75 mm. As used herein, the wearer's normal line of sight shall refer to a line projecting straight ahead of the wearer's eye, with substantially no angular deviation in either the vertical or horizontal planes. In these embodiments, a thickness of support portion 20 may be between 3.00 mm to 11.00 mm. In these embodiments, the thickness of support portion 20 may be between 1.5, 2, or 3 times the thickness of lens 10 in the ocular region. In embodiments of support portion 20 that extend rearward from rear surface 5, there is no noticeable change in perceived curvature when lens 10 is viewed from a front view, which may be desirable aesthetically and may also improve the aerodynamics of lens 10. In some embodiments, support portion 20 may be located at least partially, or completely, in the ocular region. Alternatively, in other embodiments, support portion may be located completely outside of the ocular region, as shown, for example, in FIG. 3.

In other embodiments, support portion 20 could extend forward from front surface 6 of lens 10. For purposes of this disclosure, the forward, outward, or straight-ahead direction is defined as the direction extending from the face of a wearer directly through lens 10 along or parallel with the line of sight of the wearer when the wearer is looking straight ahead. An embodiment of support portion 20 that extends forward of front surface 6 is shown, for example, with the dashed lines in the cross section view of FIG. 4. In these embodiments, support portion may extend forward of front surface 6 between 3.00 mm and 11.00 mm. These "forward-facing" embodiments of support portion 20 may be configured with any desired cross-sectional shape. Some example embodiments of possible shapes of support portion 20 that extend forward of lens 10 are described in further detail in the U.S. Patent Application No. 62/809,267 filed on Feb. 22, 2019 and titled "Eyewear Lens for Frameless Eyewear", the complete disclosure of which is incorporated herein by reference.

In other embodiments, support portion 20 may extend forward from front surface 6 and rearwards from rear surface 5. In these embodiments, the thickness of support portion 20 may be disposed symmetrically on either side of lens 10, with support portion 20 extending the same distance from each surface of lens 10. In these embodiments, each side of support portion 20 (the side extending from rear surface 5 and front surface 6, respectively) may extend between 1.50 mm and 6.50 mm from their respective surfaces, for a total thickness of between 3.00 mm and 11.00 mm. These measurements are taken relative to a continuation of the local curvature of either rear surface 5 or front surface 6 through support portion 20. In other words, the distance that support portion 20 extends from either surface is measured relative to what would be a point on that surface if support portion 20 did not exist. This measurement is illustrated, for example, in FIG. 4 as distance $t_f$. In other, related embodiments support portion 20 that extends from both surfaces of lens 10 may not extend the same distance from each surface. This may be desirable, for example, to reduce the visibility of support portion 20 from the exterior of lens 10 by reducing how far support portion 20 extends forward from front surface 6. In these embodiments, for example, support portion 20 may extend between 1.00 mm to 5.0 mm from front surface 6 and between 2.00 mm and 6.00 mm from rear surface 5.

The shape of the support portion 20 shown in FIG. 4 is rounded in cross-section, but any desired cross-section may be used. The increased thickness of support portion 20 acts to stiffen and strengthen lens 10. Embodiments of support portion 20 that extend laterally as shown in FIG. 3 are particularly helpful with increasing the lateral stiffness of lens 10, which is important for ensuring proper fit because of the way that strap 2 pulls on the lateral ends of lens 10. In all embodiments, support portion 20 is an integral part of lens 10 that is not added on separately through welding, gluing, or other methods of attachment.

In some embodiments, lens 10 does not include any extrusion, protrusion, or other elements that extend more than 5 mm, 10 mm, or 15 mm beyond either surface (front surface 6 or rear surface 5) of lens 10. In some embodiments, lens 10 does not include any extrusion, protrusion, or other elements located within 1 cm of top 16 and bottom 17 and within 5 cm of a centerline of lens 10 that extends more than 5 mm or 10 mm beyond the surface of lens 10. These extrusions or protrusion may include, for example, first strap attachment portion 12, second strap attachment portion 14, support portion 20, and cushion retainer 30.

In other embodiments, support portion 20 may be located near bottom 17 of lens 10, instead of near top 16 of lens 10. In other embodiments, support portion 20 may comprise multiple thickened sections, for example a thickened section stretching laterally near top 16 as shown in FIG. 3, and one or more horizontally-oriented thickened sections of lens 10 near bottom 17 of lens 10 as shown in FIG. 3. In some embodiments, support portion 20 may include multiple thickened sections stretching laterally near top 16 as shown in FIG. 3 (i.e. support portion 20 may be discontinuous). Any of these embodiments of support portion 20 may extend from either front surface 6, rear surface 5, or both surfaces of lens 10. Other orientations and configurations of support portion 20 may be desirable to adjust the properties of lens 10. For example, vertically-oriented thickened sections of lens 10 may be part of support portion 20 if the stiffness of lens 10 in the vertical direction (i.e. between top 16 and bottom 17) is an important property of lens 10. Accordingly, embodiments of support portion 20 may be located near the outer perimeter of lens 10, for example within one centimeter of the outer perimeter of lens 10 (i.e. top 16, bottom 17, left side 18, and right side 19). In any embodiments of support portion 20, it is desirable to place support portion 20 such that it is not visible in the field of vision of a wearer. For example, the embodiment of support portion 20 shown in FIG. 3 places the thickened section under cushion 4, where it is not visible to the wearer. In some embodiments, lens 10 has a stiffness that is greater than the stiffness of an otherwise identical lens configured for use with a separate frame or chassis.

Changing the dimensions of support portion 20 has an effect on the stiffening properties provided by support portion 20. For example and in general, when the support portion 20 has a longer length L, a height h of support portion 20 and/or a thickness of support portion 20 may be made smaller to achieve a given increase in stiffness of lens 10. Generally, embodiments of support portion 20 that extend along a greater percentage of upper portion 4 than others will result in a stiffer lens 10. In FIG. 3, support portion 20 is illustrated as being laterally centered on lens 10, which is to say that support portion 20 extends an equal distance towards left side 19 and right side 18 relative to meridian line 11. However, support portion 20 does not necessarily need to be centered, and could extend further to one side of lens 10 than to the other side.

In some embodiments, goggle 10 may be a single lens goggle, which means that there is no additional lens either in front of or behind lens 10. In these embodiments, lens 10 may have additional features to reduce the formation of condensation on rear surface 5 (commonly known as lens "fogging"), such as chemical treatment of rear surface 5 or improved ventilation of lens 10. In some embodiments, goggle 10 may be a double lens goggle, where lens 10 may, for example, be an outer lens with an addition inner lens disposed on the interior surface of lens 10.

The embodiments discussed above result in goggle 1 with lens 10 that is structurally self-supporting. Lens 10 serves as the frame or chassis for goggle 1 with the features or elements usually found on a frame created as integral, monolithic parts of lens 10. Accordingly, a truly frameless goggle 1 is achieved. Frameless goggle 1 having such built-in components according to embodiments above provides several performance benefits, including an improved aesthetic appearance, an aerodynamically streamlined shape, and reduced part count for manufacturing and assembly.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A goggle comprising a lens, the lens comprising:
    a lens body comprising:
        a first strap attachment portion at a first end of the lens body, wherein the first strap attachment portion is configured to retain a first end of a goggle strap, wherein the first strap attachment portion comprises a first protrusion that extends rearward from the lens body, and wherein the first protrusion comprises a first receptacle for receiving the first end of the goggle strap; and
        a second strap attachment portion at a second end of the lens body, wherein the second strap attachment portion is configured to retain a second end of the goggle strap, wherein the second strap attachment portion comprises a second protrusion that extends rearward from the lens body, and wherein the second protrusion comprises a second receptacle for receiving the second end of the goggle strap; and
        a frame element, wherein the frame element is a monolithic part of the lens body, and wherein the frame element increases a stiffness of the lens when compared to an otherwise identical lens without the frame element,
    wherein the lens is structurally self-supporting without a frame, and
    wherein the first strap attachment portion and the second strap attachment portion are monolithic portions of the lens body.

2. The goggle of claim 1, wherein the frame element is a support portion extending in a direction between the first end and the second end, and wherein a thickness of the lens body in the support portion is greater than a thickness of the lens body outside of the support portion.

3. The goggle of claim 2, wherein the support portion is located on an upper third of the lens body.

4. The goggle of claim 1, wherein the first strap attachment portion and the second strap attachment portion are not visible from a viewpoint directed towards a front surface of the lens, the viewpoint located along a viewpoint line extending in a straight-ahead direction from the front surface of the lens, wherein the viewpoint line intersects a meridian line that divides the lens into two equal portions, the meridian line extending along the front surface of the lens in a direction between a top of the lens and a bottom of the lens.

5. The goggle of claim 1, wherein the goggle strap is attached to the first strap attachment portion at the first end of the goggle strap and is attached to the second strap attachment portion at the second end of the goggle strap, wherein the goggle strap is configured to form a closed loop with the lens; and
    a cushion attached to an inner surface of the lens, wherein the cushion is configured to contact a face of a user when the goggle is being worn by the user.

6. The goggle of claim 1, wherein the lens does not comprise any protrusions that extend more than 15 mm from a front surface or a rear surface of the lens.

7. A goggle, comprising:
    a lens;
    a cushion retainer located on an interior surface of the lens that is an integral and monolithic part of the lens, wherein the cushion retainer increases a stiffness of the lens when compared to an otherwise identical lens without the cushion retainer, the cushion retainer formed as a protrusion extending from the interior surface of the lens;
    a support portion disposed on the interior surface of the lens that is an integral part of the lens, wherein the support portion extends from the interior surface and has a curved surface at its distal end; wherein the support portion increases a stiffness of the lens when compared to an otherwise identical lens without the support portion; and
    a cushion attached to the cushion retainer, wherein the cushion is configured to contact a face of a user when the goggle is being worn,
    wherein the lens with the support portion is structurally self-supporting without a frame.

8. The goggle of claim 7, wherein at least a part of the support portion is disposed outside of an ocular region of the lens, and wherein a part of the lens that is inside the ocular region is less thick than the part of the support portion.

9. The goggle of claim 7, wherein the support portion is located on an upper third of the lens.

10. The goggle of claim 7, wherein a first attachment point and a second attachment point are not visible from a viewpoint located along a viewpoint line extending in a straight-ahead direction from the lens, wherein the viewpoint line intersects a meridian line that divides the lens into two equal portions, the meridian line extending along a front surface of the lens in a direction between a top of the lens and a bottom of the lens.

11. The goggle of claim 7, further comprising:
a first strap attachment portion integrally molded at a first end of the lens, wherein the first strap attachment portion is configured to retain a first end of a strap; and
a second strap attachment portion integrally molded at a second end of the lens that is opposite the first end, wherein the second strap attachment portion is configured to retain a second end of the strap.

12. The goggle of claim 11, wherein the strap is connected to the first attachment point at the first end of the strap and is connected to the second attachment point at the second end of the strap.

13. The goggle of claim 11, wherein the first strap attachment portion and the second strap attachment portion are not visible from a viewpoint located along a viewpoint line extending in a straight-ahead direction from the lens, wherein the viewpoint line intersects a meridian line that divides the lens into two equal portions, the meridian line extending along the front surface of the lens in a direction between a top of the lens and a bottom of the lens.

14. A goggle, comprising:
a lens;
a cushion retainer integral and monolithic to a rear surface of the lens configured to retain a cushion;
a first strap attachment portion integrally molded at a first end of the lens, wherein the first strap attachment portion is configured to retain a first end of a strap, and wherein the first strap attachment portion is closer to the first end than the cushion retainer; and
a second strap attachment portion integrally molded at a second end of the lens that is opposite the first end, wherein the second strap attachment portion is configured to retain a second end of the strap, and wherein the second strap attachment portion is closer to the second end than the cushion retainer; and
the cushion attached to the rear surface of the lens and the cushion retainer, wherein the cushion is configured to contact a face of a user when the goggle is being worn, wherein the lens is structurally self-supporting without a frame, and
wherein the first strap attachment portion and the second strap attachment portion are not visible from a viewpoint directed towards a front surface of the lens, the viewpoint located along a viewpoint line extending in a straight-ahead direction from the front surface of the lens, wherein the viewpoint line intersects a meridian line that divides the lens into two equal portions, the meridian line extending along the front surface of the lens in a direction between a top of the lens and a bottom of the lens.

15. The goggle of claim 14, further comprising a support portion that is an integral part of the lens, wherein the support portion is configured to increase the stiffness of the lens.

16. The goggle of claim 15, wherein a thickness of the support portion is greater than a thickness of a region of the lens without the support portion.

17. The goggle of claim 16, wherein the support portion is located on an upper third of the lens.

18. The goggle of claim 15, wherein the support portion is located on an upper third of the lens.

19. The goggle of claim 15, wherein the strap is attached to the first strap attachment portion at the first end of the strap and is attached to the second strap attachment portion at the second end of the strap, wherein the strap is configured to form a closed loop with the lens.

20. The goggle of claim 15, wherein the lens does not comprise any protrusions that extend more than 15 mm from the front surface or the rear surface of the lens.

21. The goggle of claim 15, wherein at least a part of the support portion is disposed outside of an ocular region of the lens, and wherein a part of the lens that is located in the ocular region is less thick than the part of the support portion.

22. A goggle, comprising:
a lens;
a cushion retainer located on an interior surface of the lens that is an integral and monolithic part of the lens, the cushion retainer disposed at a nose region of the lens, wherein the cushion retainer increases a stiffness of the lens when compared to an otherwise identical lens without the cushion retainer;
a support portion disposed on the interior surface of the lens that is an integral part of the lens, the support portion disposed at a brow region of the lens, wherein the support portion increases a stiffness of the lens when compared to an otherwise identical lens without the support portion; and
a cushion attached directly to the cushion retainer, wherein the cushion is configured to contact a face of a user when the goggle is being worn, and
wherein the lens with the support portion is structurally self-supporting without a frame.

23. The goggle of claim 22, further comprising:
a first strap attachment portion integrally molded at a first end of the lens, the first strap attachment portion having a first protrusion extending rearwards from the lens with a first receptacle disposed in the first protrusion for receiving a first end of a strap; and
a second strap attachment portion integrally molded at a second end of the lens that is opposite the first end, the second strap attachment portion having a second protrusion extending rearwards from the lens with a second receptacle disposed in the second protrusion for receiving a second end of the strap.

24. The goggle of claim 22, wherein at least a part of the support portion is disposed outside of an ocular region of the lens, and wherein a part of the lens that is inside the ocular region is less thick than the part of the support portion.

25. The goggle of claim 23, wherein the first strap attachment portion and the second strap attachment portion are not visible from a viewpoint located along a viewpoint line extending in a straight-ahead direction from the lens, wherein the viewpoint line intersects a meridian line that divides the lens into two equal portions, the meridian line extending along a front surface of the lens in a direction between a top of the lens and a bottom of the lens.

* * * * *